(12) United States Patent
Edic et al.

(10) Patent No.: US 7,742,563 B2
(45) Date of Patent: Jun. 22, 2010

(54) X-RAY SOURCE AND DETECTOR CONFIGURATION FOR A NON-TRANSLATIONAL X-RAY DIFFRACTION SYSTEM

(75) Inventors: Peter Michael Edic, Albany, NY (US); Geoffrey Harding, Hamburg (DE); Bruno K. B. De Man, Clifton Park, NY (US); Helmut Rudolf Strecker, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 0 days.

(21) Appl. No.: 12/207,641

(22) Filed: Sep. 10, 2008

(65) Prior Publication Data

US 2010/0061512 A1 Mar. 11, 2010

(51) Int. Cl.
*G01N 23/20* (2006.01)
*G01N 23/04* (2006.01)
(52) U.S. Cl. .............................. 378/70; 378/71; 378/57
(58) Field of Classification Search ...................... 378/6, 378/7, 19, 70, 71, 86–90, 98.8
See application file for complete search history.

(56) References Cited

U.S. PATENT DOCUMENTS 6,693,988 B2 2/2004 Harding
6,917,667 B2 7/2005 Fujinawa et al.
7,092,485 B2 8/2006 Kravis
2002/0097836 A1* 7/2002 Grodzins ...................... 378/57

FOREIGN PATENT DOCUMENTS

WO 2005010512 A1 2/2005
WO 2007149751 A2 12/2007

* cited by examiner

*Primary Examiner*—Irakli Kiknadze
(74) *Attorney, Agent, or Firm*—Armstrong Teasdale LLP

(57) ABSTRACT

A system and method for scanning objects using a non-translational x-ray diffraction (XRD) system is disclosed. The system includes a scanning area through which an object to be scanned traverses and a distributed x-ray source having a plurality of focal spot locations. The distributed x-ray source is affixed on the scanning area and is configured to emit x-rays towards the object as a series of parallel x-ray beams. A stationary detector arrangement is affixed on another side of the scanning area generally opposite the distributed x-ray source and is configured to measure a coherent scatter spectra of the x-rays after passing through the object. A data acquisition system (DAS) is connected to the detector arrangement and is configured to measure the coherent scatter spectra, which is utilized to generate XRD data and determine a material composition of at least a portion of the object from the XRD data.

23 Claims, 4 Drawing Sheets

X-RAY SOURCE AND DETECTOR CONFIGURATION FOR A NON-TRANSLATIONAL X-RAY DIFFRACTION SYSTEM

BACKGROUND OF THE INVENTION

Embodiments of the invention relate generally to x-ray diffraction (XRD) systems and, more particularly, to an x-ray source and detector configuration in a non-translational XRD system.

In recent years, the detection of contraband, such as explosives, being transported in luggage and taken onto various means of transportation has become increasingly important. To meet the increased need for such detection, advanced Explosives Detection Systems (EDSs) have been developed that can not only detect suspicious articles being carried in the luggage but can also determine whether or not the articles contain explosive materials.

These detection systems, at a minimum, include computed tomography (CT) machines that are capable of acquiring mass and density information (as well as additional information, such as an effective atomic number) on items within luggage. To acquire more detailed and highly selective information on luggage being scanned, explosives detection devices based on x-ray diffraction (XRD) can be employed in combination with the CT system to provide complementary information relative to the data from the CT system, thereby improving the overall detection performance of the EDS. That is, the complementary information gained from the XRD system, when combined with the CT data, can provide higher detection sensitivity with reduced false alarms as compared to CT data alone, thus resulting in less manual or follow-on inspection needed to clear the alarms and preventing inspection system backup.

Commercial designs of XRD systems, however, limit the throughput achievable in existing EDSs that combine various scanning and detection technologies. That is, XRD systems presently in use typically emit a highly collimated X-ray beam that is small in diameter toward a region of interest (ROI) in an object to be interrogated. To investigate additional ROIs in the object, the object has to be repositioned and/or the x-ray source and detector combination has to be mechanically repositioned to illuminate the new ROI. This repositioning of either the object or of the collimator/detector arrangement in the system can lead to increased scanning time and greatly reduce baggage scanning rates.

Therefore, it would be desirable to design an apparatus and method for reducing the scanning time of objects in an XRD system. It would also be desirable to control the XRD system to interrogate ROIs in the object based on data acquired from a separate imaging system to further increase efficiency in operation of the XRD system.

SUMMARY

Embodiments of the invention are directed to a method and apparatus for scanning objects using x-ray diffraction (XRD) that overcome the aforementioned challenges. An XRD system is disclosed that includes a stationary x-ray source and detector configuration. The stationary x-ray source projects a series of parallelly arranged x-rays toward the object and the stationary detector arrangement. The stationary detector arrangement measures a coherent scatter spectra of the x-rays after passing through the object.

According to an aspect of the invention, a non-translational x-ray diffraction (XRD) system includes a scanning area configured to receive an object to be scanned that traverses through the scanning area, a distributed x-ray source affixed on one side of the scanning area to emit x-rays towards the object and including a plurality of x-ray focal spot locations. The distributed x-ray source is configured to emit the x-rays as a series of parallel x-ray beams. The non-translational XRD system also includes a stationary detector arrangement affixed on another side of the scanning area generally opposite the distributed x-ray source that is configured to measure a coherent scatter spectra of the x-rays after passing through the object and a data acquisition system (DAS) connected to the detector arrangement and configured to measure the coherent scatter spectra, which is utilized to generate XRD data and determine a material composition of at least a portion of the object from the XRD data.

According to another aspect of the invention, a method for detecting contraband includes the steps of positioning an object within a field of view in an x-ray diffraction (XRD) system and generating primary x-rays from a stationary x-ray source in the XRD system to scan the object, wherein the primary x-rays are generated as parallel x-ray beams. The method also includes the steps of receiving coherently scattered x-rays from the primary x-rays with a stationary detector arrangement to generate XRD data and determining the probability of contraband being present in the object by analyzing the XRD data.

According to yet another aspect of the invention, a contraband detection system includes a non-translational x-ray diffraction (XRD) system having a gantry with an opening to receive an object to be scanned that traverses through the gantry along an axis of translation and a stationary distributed x-ray source affixed on one side of the gantry and having a plurality of x-ray focal spot locations in a linear arrangement configured to project x-rays toward the object. The non-translational XRD system also includes a stationary detector arrangement affixed on another side of the gantry and generally opposite the stationary distributed x-ray source and configured to measure a coherent scatter spectra of the x-rays after passing through the object, the stationary detector arrangement comprising at least one detector having a linear configuration substantially similar to the linear arrangement of the plurality of x-ray focal spot locations. A data acquisition system (DAS) is also included in the non-translational XRD system and is connected to the detector arrangement and configured to measure the coherent scatter spectra, which is utilized to determine a material composition of at least a portion of the object.

These and other advantages and features will be more readily understood from the following detailed description of preferred embodiments of the invention that is provided in connection with the accompanying drawings.

DETAILED DESCRIPTION OF PREFERRED EMBODIMENTS

Figure 1:
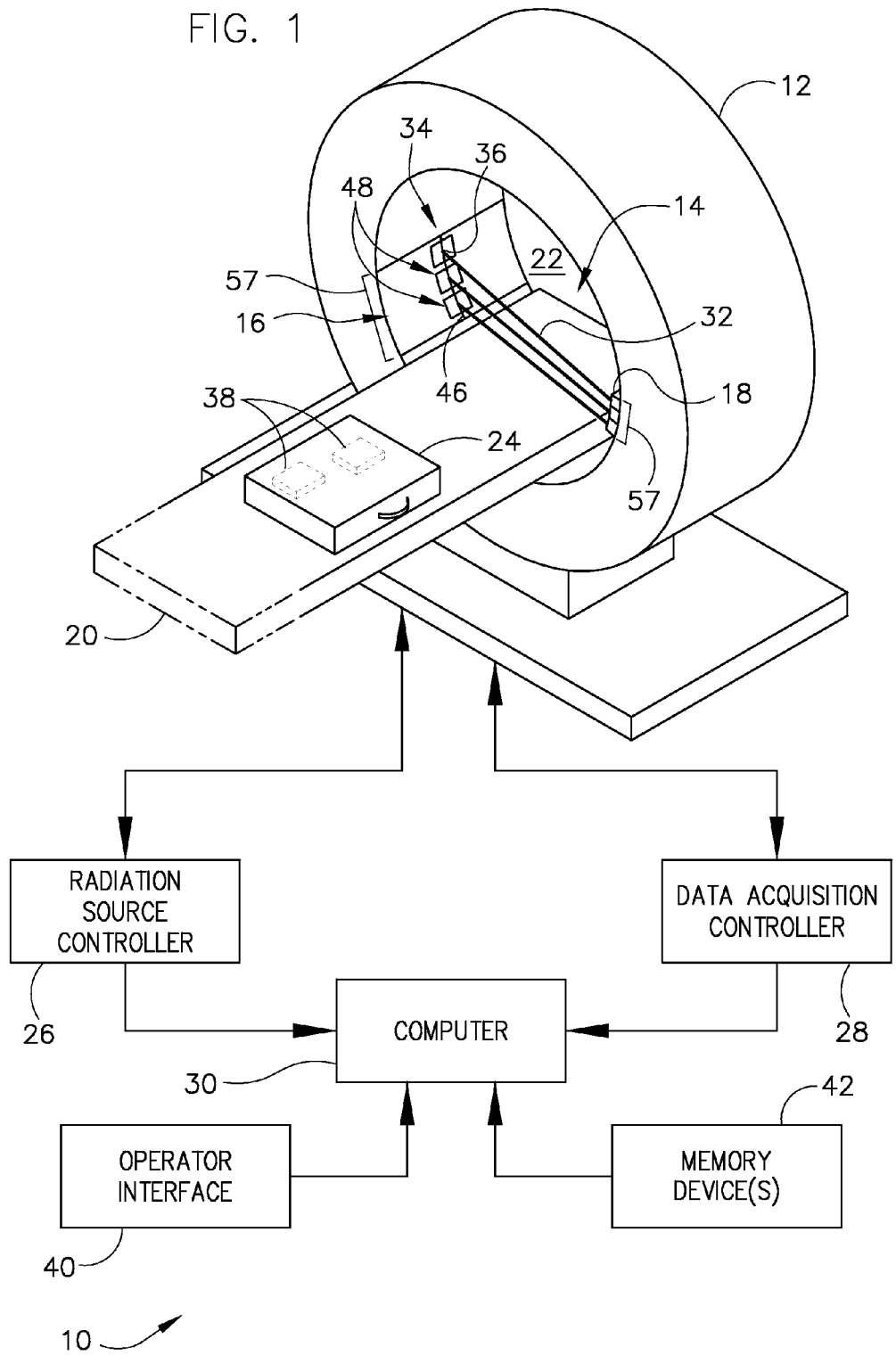
FIG. 1 is a schematic diagram of an x-ray diffraction system according to an embodiment of the invention.

Referring to FIG. 1, an isolated view of x-ray diffraction (XRD) system 10 is illustrated. The XRD system 10 comprises a gantry 12 that generally defines a scanning area 14 and has positioned thereon a stationary source of x-ray radiation 16 and a stationary detector arrangement 18 each fixed on gantry 12. The XRD system 10 is configured to receive a conveyor belt 20 through a bore 22 in gantry 12 to allow, for example, the passage of baggage items 24 therethrough.

To control operation of x-ray source 16 and detector arrangement 18, the XRD system 10 includes a radiation source controller 26 and a data acquisition controller 28, which may both function under the direction of a computer 30. The radiation source controller 26 may receive inputs from operator input to the computer 30 or may utilize additional sensor information, such as suspicious regions-of-interest identified by CT scans, X-ray scans, trace acquisitions, etc. The radiation source controller 26 regulates timing and location for discharges of x-ray radiation 32, which is directed from the x-ray source 16 toward the detector arrangement 18 positioned on an opposite side of gantry 12. The radiation source controller 26 may trigger a cathode module 34 having one or more emitters 36 positioned thereon in the x-ray source 16 at each instant in time for acquiring multiple x-ray diffraction data. In certain arrangements, for example, the x-ray radiation source controller 26 may trigger emission of radiation in sequences from different emitter elements 36 in x-ray source 16, as will be explained in detail below. In addition, although in a preferred embodiment the stationary x-ray source 16 is comprised of one or more field emission devices, the electron beams can be generated from one of many types of electron emitters, such as thermionic cathodes. Moreover, one or more single electron beams can be generated and steered using electromagnetic or electrostatic fields to generate multiple x-ray focal spot locations, while still maintaining the stationary nature of the source.

The x-rays 32 sent from x-ray source 16 pass through one or more ROIs 38 in baggage item 24, are diffracted by the specific material present in the ROI 38, and are directed onto the detector arrangement 18, which measures the coherent scatter spectra of the x-rays after passing through the ROI 38 to acquire "XRD data." In one embodiment of the invention, the coherent scatter spectra of the x-rays may then be processed and compared to a library of known reference spectra for various dangerous substances (i.e., explosives, narcotics, etc.) that can be stored on computer 30. As such, a signature for the molecular structure of a material in the ROI 38 can be analyzed and a determination made to discern if that structure corresponds to a known explosive material, contraband items (narcotics, etc.), or other item of interest. Many such measurements may be collected in an examination sequence, and data acquisition controller 28, which is coupled to detector arrangement 18, receives signals from the detector arrangement 18 and processes the signals and/or sends the requisite data to computer 30, thus acquiring the XRD data.

Computer 30 generally regulates the operation of the radiation source controller 26 and the data acquisition controller 28. The computer 30 may thus cause radiation source controller 26 to trigger emission of x-ray radiation 32, as well as to coordinate such emissions during imaging sequences defined by the computer 30. The computer 30 also receives data acquired by data acquisition controller 28 and coordinates storage and processing of the data. An operator interface 40 may be integral with the computer 30 and will generally include an operator workstation for initiating imaging sequences, controlling such sequences, and manipulating data acquired during imaging sequences, which can be stored in a memory device 42.

Figure 2:
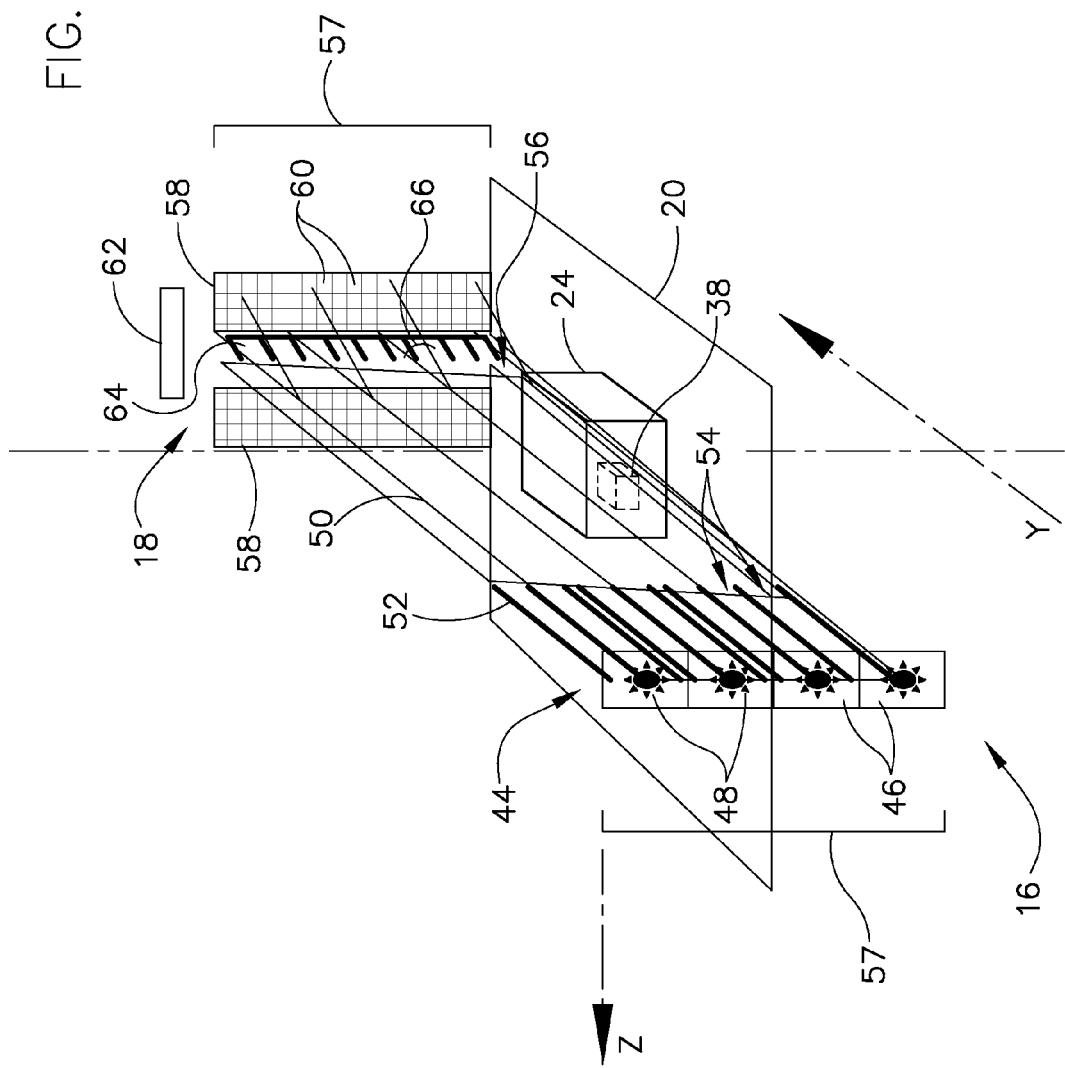
FIG. 2 is illustrative of a stationary distributed x-ray source and diffraction detector for use with the system of FIG. 1 according to one embodiment of the invention.

Referring now to FIG. 2, an x-ray source 16 and detector arrangement 18 of the type that may be employed in the stationary XRD system 10 is shown, according to one embodiment of the invention. The x-ray source 16 is in the form of a distributed x-ray source that may include one or more cathode modules 44, with each cathode module 44 comprising one or more electron beam emitters 46 that are positioned at focal spot locations 48 and coupled to radiation source controller 26 (shown in FIG. 1) by way of activation connections (not shown). Emitters 46 are triggered by the source controller 26 during operation of the XRD system 10. Emitters 46 are positioned facing an anode (not shown) and, upon triggering by the source controller 26, the emitters 46 emit electron beams toward the anode. Upon striking of the electron beams on the anode, which may, for example, be a tungsten rail or element, a primary beam of x-ray radiation 50 is emitted, as indicated at reference numeral 50. The primary x-ray beams 50 are directed, then, toward a primary collimator 52, which is generally opaque to the x-ray radiation, but which includes apertures 54. The apertures 54 may be fixed in dimension, or may be adjustable, to permit primary x-ray beams 50 to penetrate through the primary collimator 52 to form focused, collimated primary x-ray beams. The primary x-ray beams 50 are directed to an imaging volume 56 (i.e., scanning area) of the XRD scanner 10, pass through one or more ROIs 38, and are diffracted to impact detector arrangement 18 on an opposite side of the XRD scanner 10.

As shown in FIG. 2, distributed x-ray source 16 and detector arrangement 18 are configured to form a parallel-beam XRD arrangement. That is, emitters 46 of x-ray source 16 are distributed in a linear pattern at a point on the Z axis, so as to extend along the imaging plane 56, in the "in-plane direction." The plurality of emitters 46 are distributed to form a distributed x-ray source 16 having a length 57. Detector arrangement 18 includes one or more detectors 58 having a generally linear configuration in one embodiment, that is substantially similar to the arrangement of the emitters 46 (i.e., detectors 58 have a length 57 approximately equal to the x-ray source 16) and that are positioned to receive a plurality of "parallel" x-ray beams emitted by the linear distributed x-ray source 16. More specifically, the one or more rows of stationary detectors 58 are oriented along the z-axis, parallel to the direction of baggage throughput, and each of the detectors 58 is comprised of a plurality of detector elements 60, which receive the radiation emitted by the linear distributed x-ray source 16 and diffracted by a material in ROI 38. Signal processing circuitry, such as an application specific integrated circuit (ASIC) 62, is associated with each detector 58. Detector elements 60 can be configured to have varying resolution so as to satisfy a particular imaging application. A secondary collimator 64 is positioned adjacent to detectors 18 that allows the detector elements 60 to measure only radiation at a constant scatter angle 66 with respect to the orientation of the primary x-ray beams 50 emitted from the distributed x-ray source 16 (i.e., within a certain scatter angle range).

In one embodiment, detectors 18 are also configured for energy resolution less than 5% at an x-ray photon energy of 60 keV and can be energy sensitive detectors comprised of high-purity germanium, CZT, or other suitable energy sensitive detector technology. Secondary collimators 64 may restrict the field of view of detectors 60 having identical X coordinate to coherent scatter generated by primary beam 50 sharing this X coordinate and also code the Y coordinate of the scatter voxel onto the Z coordinate of the detector 60 by virtue of the constant angle property of the secondary collimator, thus allowing measurement of a diffraction signal from a particular region of interest of baggage 24.

As described above, cathode modules 44, and corresponding emitters 46, within linear distributed x-ray source 16 are independently and individually addressable so that radiation can be triggered from each of the focal spot locations 48 at points in time as needed. The triggering of a particular cathode module 44 and its emitters 46 is determined by the one or more ROIs 38 identified in the baggage item 24. According to one embodiment of the invention, and as set forth in detail below, ROIs 38 can be identified in the baggage item 24 via data previously acquired by another imaging system, such as a CT scanner (not shown). The ROIs 38 can be identified by way of an analysis of CT data (e.g., 2D segmentation or limited 3D segmentation of reconstructed data) and the mass, density, and/or effective atomic number characteristics in the CT data that may be indicative of an explosive material or some other object of interest. These identified ROI(s) 38 within the baggage item 24 can then be mapped to determine where the ROI 38 lie within the field-of-view 56 and this data can be passed onto XRD system 10. As mentioned previously, focal spot locations 48 can be effected by one or more electron beams that are directed through electrostatic or magnetic means to the appropriate location on the anode (not shown).

In selecting activation of a desired emitter 46 at a focal spot location 48 in distributed x-ray source 16, data related to the location of the ROI 38 within the field-of-view 52 are sent to computer 30 (shown in FIG. 1). A desired emitter 46 is then selected/activated based on its proximity to the ROI 38, with the emitter 46 that provides an x-ray beam that traverses ROI 38 being activated. More precisely, an emitter 46 at a focal spot location 48 is selected from the plurality of emitters in the cathode module 44 of linear distributed x-ray source 16 whose resulting primary x-ray beam 50 most overlaps a centroid of the ROI 38 (i.e., most closely intersects the ROI). If more than one ROI 38 is identified in the baggage item 20, an activation sequence is determined (by computer 30) in which a plurality of the emitter elements 46 at focal spot locations 48 are sequentially activated or queued in a desired activation order, with the selection/activation of each emitter 46 based on the overlap of its primary x-ray beam with a respective ROI 38. The computer 30 queues the activation of emitters 46 based on their association with the ROI 38 and the location of the ROI 38 within baggage item 24 (and field-of-view 56) to optimize a scanning process in the XRD scanner 10 and to achieve a maximum throughput rate of baggage 24 through XRD scanner 10. Beneficially, as no rotation or repositioning of an x-ray source/detector arrangement is required, but only electrical activation of selected emitters 46 in the linear distributed x-ray source 16, no time delay for x-ray source/detector re-positioning is experienced.

While described above as being individually or sequentially activated, in other configurations, the emitters 46 are addressable in logical groups. For example, pairs or triplets of emitters 46 may be logically "wired" together. Where desired, and as determined by the identified ROI 38, more than one such group of emitters 46 may be triggered concurrently at any instant in time.

Beneficially, the parallel beam configuration of x-rays generated by distributed x-ray source 16 and received by detector arrangement 18 allows for an x-ray source of smaller size to be implemented in XRD system 10 as compared to inverse geometry configurations (i.e., large x-ray source, point detector). Thus, the overall size of XRD system 10 can also be greatly reduced such that the XRD system can be used in small object scanning applications, such as at airport checkpoints. In one embodiment, distributed x-ray source 16 and detector arrangement 18 (i.e., detectors 58) are each approximately 0.5 meters in length, although it is also envisioned that smaller source/detector combinations could also be implemented. Additionally, while x-ray source 16 and detector arrangement 18 are described above as being identical in size, it is also recognized that detector arrangement 18 could be slightly larger than x-ray source 16 (e.g., 0.1 m), so long as the length 57 of detector arrangement 18 is sufficient to receive each of the parallelly emitted x-ray beams 50 from x-ray source 16.

Figure 3:
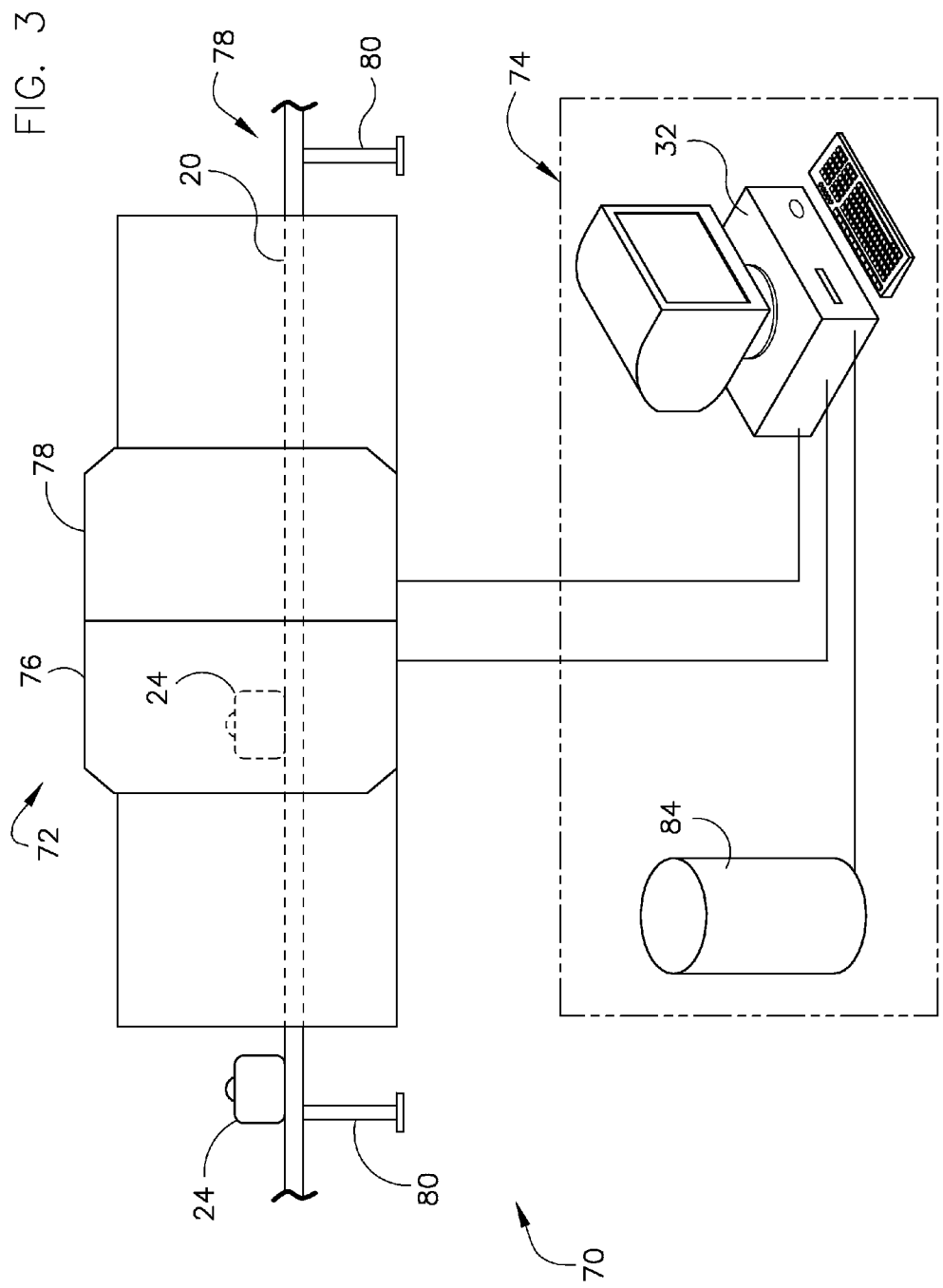
FIG. 3 illustrates a contraband detection system according to an embodiment of the invention.

Referring to FIG. 3, a contraband detection system 70 (i.e., explosives detection system (EDS) 70) is shown incorporating an XRD system, such as those set forth above with respect to FIGS. 1 and 2. Although specific mention of an EDS 70 is provided in preferred embodiments described below, other contraband detection systems such as for narcotics, knives, guns, etc. are contemplated. EDS 70 includes a scanning subsystem 72 and a computer subsystem 74. The scanning subsystem 72 includes a first scanner system 76 (i.e., first contraband/explosives detection apparatus) and a second scanner system 78 in the form of an XRD system. The first scanner system 76 can include, but is not limited to, any of a computed tomography (CT) scanner, a quadrupole resonance (QR) scanner, or any other contraband scanner (e.g., trace detection system). As shown in FIG. 3, XRD system 78 is positioned in-line with first scanner system 76, to receive luggage, baggage, or other objects of interest 24 directly therefrom. While first scanner system 76 and XRD system 78 are shown as a physically integrated EDS 70, the EDS may be separate entities placed in close proximity to one another. In such an arrangement, however, the systems must maintain registration of the spatial coordinate system to facilitate overall system scanning operations. If registration is not maintained, special techniques may be required to determine object orientation and define the appropriate ROI 38 that needs to be scanned. Furthermore, the data acquired from both systems is also integrated/shared to increase the throughput of baggage 24 through the EDS 70 and the overall threat detection performance. Although both scanning systems 76, 78 can be configured to scan the entire baggage item 24 and the data retrospectively evaluated for overall threat assessment, the queuing of subsequent scanning systems by data acquired from the first scanning system 76 facilitates overall system throughput by identifying suspicious regions of interest in the baggage item 24.

A conveyor system 78 is also provided and includes conveyor belt 20 supported by a structure 80 to automatically and continuously pass packages or baggage pieces 24 through passageways extending through both the first scanner system 76 and XRD system 78 such that a throughput of baggage items 24 for scanning in first scanner system 76 and XRD system 78 is provided. Baggage items 24 are fed through first scanner system 76 and XRD system 78 by conveyor belt 20 while imaging data is acquired, and the conveyor belt 20 moves the baggage items 24 through the scanners 76, 78 in a controlled and continuous manner. As a result, postal inspectors, baggage handlers, and other security personnel may non-invasively inspect the contents of baggage 24 for explosives, knives, guns, narcotics, contraband, etc. Conveyor belt 20 passes baggage items 24 in a manner that preserves the relative position of baggage item 24 and contents therein, such that XRD system 78 examines locations within baggage items 24 at a coordinate location identified/flagged by first scanner system 76.

Referring still to FIG. 3, the computer subsystem 74 of EDS 70 includes a computer 82 and an electronic database 84, which is connected to the computer 82. Computer 82 is connected to both of first and second scanner systems 76, 78 to receive data therefrom and send data thereto. It is envisioned that computer subsystem 82 controls operation of both the first and second scanner systems 76, 78, as is shown in FIG. 3; however, it is also contemplated that separate computers (such as computer 30 in FIG. 1) be associated with each imaging device and be connected via a network (not shown) to provide data to computer subsystem 74.

In one embodiment, first scanner system of EDS 70 comprises a CT scanner 76 and second scanner system of EDS 70 comprises an XRD scanner 78. Based on object data acquired by CT scanner 76, regions of interest (ROI) 38 (shown in FIG. 1) in the baggage 24 having mass and/or density characteristics that may possibly correspond to a known explosive material can be identified. These ROIs 38 are identified for further examination in the XRD system to better quantify the likelihood of an explosive material being present in the baggage item 20. That is, as set forth above, the XRD system acquires and processes coherent scatter spectra of the x-rays after passing through the baggage to determine a signature for the molecular structure of a material in the ROI 38. This molecular signature is compared to a library of known reference spectra for various dangerous substances (i.e., explosives) that can be stored on a computer and a probablistic determination made to discern if that structure corresponds to a known explosive material.

Based on the acquired CT data (mass, density, and/or effective atomic number) and XRD data (spectral signature indicative of the molecular structure, noted as "molecular signature), a "Threat Status" for one or more ROI 38 in a particular piece of baggage 24 can be generated. That is, a determination can be made of the probability and/or likelihood of an explosive material being present in the baggage item 24. Toward this end, computer subsystem 74 (shown in FIG. 1) has programmed thereon a common set of threat categories, which in one embodiment can mirror the Transportation Security Administration's categorization of explosives. Each of these threat categories contains information on mass, density, effective atomic number, and molecular signature characteristics that are specific to explosives in that category.

In combining the mass, density, effective atomic number, and molecular signature characteristics obtained in the CT data and XRD data for an identified ROI, a Bayesian Data Fusion Protocol, employing Bayes' law, can be implemented. That is, the risk calculus and determination of a probability/likelihood of contraband/explosives may be characterized by Bayesian probability theory wherein the initial risk values are probabilities of the presence of each type of contraband based on a first type of scan. The probabilities are modified using Bayes' rule, with the initial risk values of the first scan being applied to and combined with risk values ascertained from scanning results of a second type of scan, to output a final risk value that is the combination of probabilities for the given types of contraband/explosives based on the combination of scans. The combination of probabilities, and corresponding final risk value, are output as the Threat Status. Although not described herein, statistical techniques other than those based on Bayesian statistics are contemplated as being useful for combining the data from multiple scanning devices.

Figure 4:
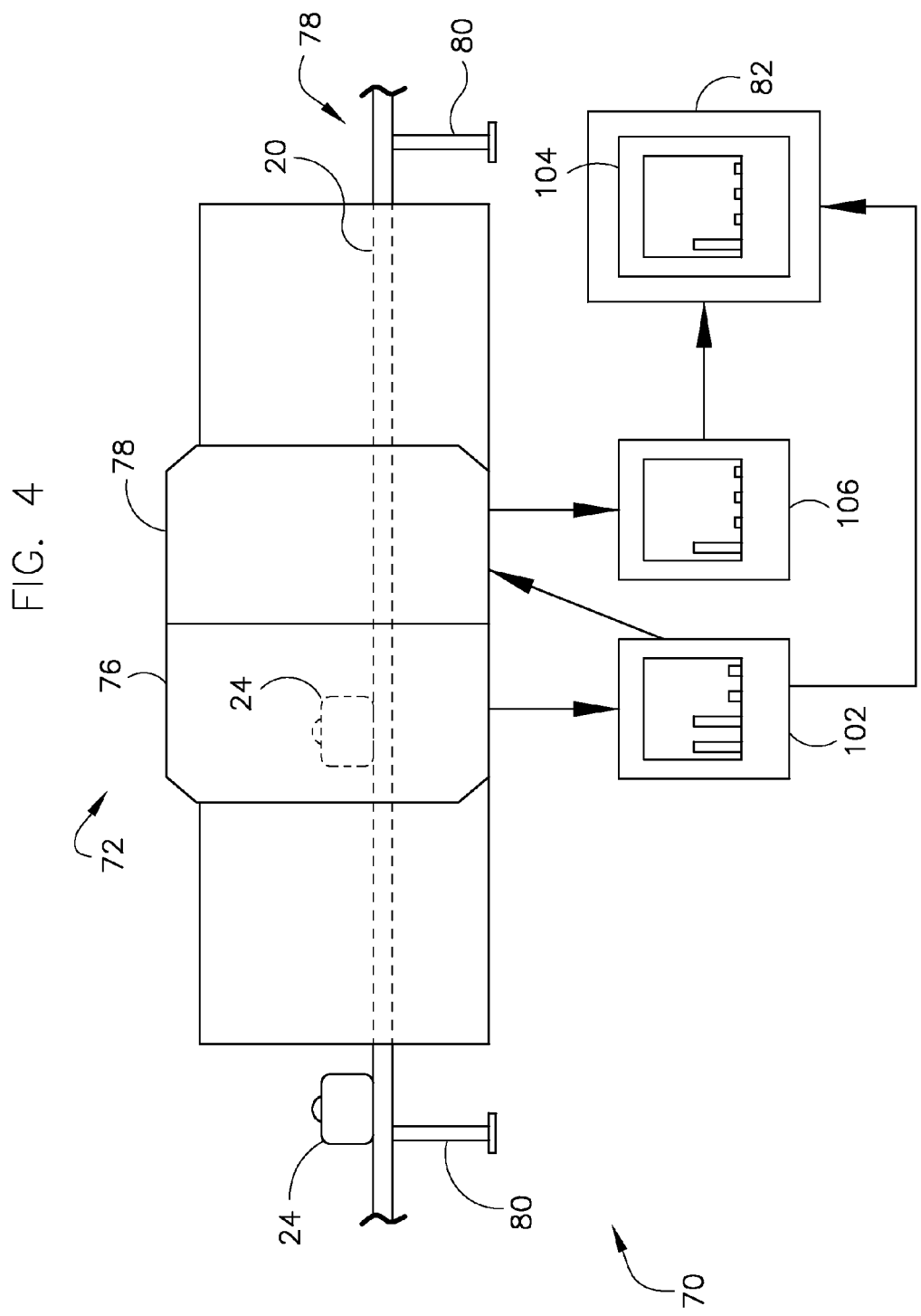
FIG. 4 is a schematic of the Explosives Detection System of FIG. 3, illustrating generation and modification of a Threat State for a baggage item.

Referring now to FIG. 4, a graphical representation of EDS 70 and the use of a Bayesian Data Fusion Protocol to determine a Threat Status is illustrated. CT data is acquired for an item of baggage 24 via CT scanner 76, whereby at least one of mass, density, and effective atomic number characteristics for the baggage 24 are determined from the acquired CT data. A preliminary threat state 102 is output for each ROI identified in the baggage item 24. The preliminary threat state 102 includes probabilities that the baggage item 24 includes the various types of contraband/explosives that are included in the pre-defined threat categories. The preliminary threat state 102 can be shown on a display device 104 of the computer 82.

The conveyor belt 20 then moves the baggage item 24 into the XRD scanner 78, which scans any ROI in the baggage item 24, as described in detail above. As illustrated in FIG. 4, the preliminary threat state 102 is sent to the XRD scanner 78, which, based on molecular signatures acquired for materials in the ROI, modifies the preliminary threat state 102 to generate an updated or final threat state 106, depending on the number of scanners/sensors in the system. The final threat state 106 includes a plurality of modified probabilities/likelihoods that the baggage item 24 includes one of the various types of contraband/explosives included in the preliminary threat states. The final threat state 106 can also then be shown on display device 104 of computer 82.

The computer 82 reads the final threat state 106 and, if the total probability of any type of contraband being in the baggage item 24 is above the critical probability for any particular threat category, the computer 82 triggers an alarm to alert an operator of the EDS 70 of the likely presence of contraband/explosives. The alarm could be one of a visual alarm displayed on computer 82, an audio alarm, or a means for extracting the suspect baggage item from the normal stream of baggage.

A technical contribution for the disclosed method and apparatus is that it provides for a computer implemented method and apparatus that increases throughput scanning capability for baggage or other objects of interest by identifying regions of interest in the baggage and providing scanning instructions to a stationary/non-translational XRD system.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while explosives detection techniques are discussed above, the invention encompasses other types of contraband, such as concealed weapons and narcotics. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A non-translational x-ray diffraction (XRD) system, comprising:

a scanning area configured to receive an object to be scanned, the object traversing through the scanning area;

a distributed x-ray source affixed to a first side of the scanning area and configured to emit x-rays towards the object, the distributed x-ray source including a plurality of x-ray focal spot locations, the distributed x-ray source configured to emit the x-rays as a series of parallel x-ray beams;

a stationary detector affixed to a second side of the scanning area generally opposite the distributed x-ray source, the stationary detector configured to measure a coherent scatter spectra of the x-rays after passing through the object;

a secondary ray collimator positioned between the object and the stationary detector, the secondary ray collimator configured to allow only scattered x-rays within a certain scatter angle range to be received at the stationary detector; and a data acquisition system (DAS) connected to the stationary detector and configured to measure the coherent scatter spectra, the coherent scatter spectra utilized to generate XRD data and to determine a material composition of at least a portion of the object from the XRD data.

2. The non-translational XRD system of claim 1, wherein the plurality of x-ray focal spot locations in the distributed x-ray source are in a linear arrangement, the distributed x-ray source configured to emit the x-rays within an imaging plane and toward the stationary detector; and wherein the stationary detector comprises at least one detector in a linear arrangement substantially similar to the linear arrangement of the plurality of x-ray focal spot locations, the at least one detector positioned to receive the scattered x-rays after passing through the object.

3. The non-translational XRD system of claim 2, wherein the at least one detector comprises a first detector and a second detector equally and oppositely offset from the distributed x-ray source.

4. The non-translational XRD system of claim 2, wherein a length of the distributed x-ray source is equal to a length of the stationary detector.

5. The non-translational XRD system of claim 4, wherein the length of the distributed x-ray source and the length of the stationary detector are each approximately 0.5 meters or less.

6. The non-translational XRD system of claim 1, comprising a computer programmed to:

receive object data from an imaging system;

identify at least one region of interest (ROI) in the object based on the object data, the at least one ROI comprising at least a portion of the object; and cause the non-translational XRD system to scan the at least one ROI.

7. The non-translational XRD system of claim 6, wherein the computer is further programmed to combine the object data from the imaging system and the XRD data to detect a presence of contraband in the object and, if the contraband is detected, assign a threat level and generate an alert.

8. The non-translational XRD system of claim 6, wherein the computer is programmed to activate at least one x-ray focal spot location of the plurality of x-ray focal spot locations based on the at least one ROI, the at least one x-ray focal spot location emitting an x-ray beam that most closely intersects a centroid of the at least one ROI as compared to x-ray beams emitted from other x-ray focal spot locations of the plurality of x-ray focal spot locations.

9. The non-translational XRD system of claim 6, wherein, when the at least one ROI comprises a plurality of ROIs, the computer is programmed to activate the plurality of x-ray focal spot locations of the distributed x-ray source in one of a queued activation pattern, a sequential activation pattern, and a concurrent activation pattern.

10. The non-translational XRD system of claim 1, further comprising a primary ray collimator positioned between the object and the distributed x-ray source.

11. The non-translational XRD system of claim 1, wherein the distributed x-ray source comprises one mere of at least one electron emitter and at least one steered electron beams beam to generate the plurality of x-ray focal spot locations.

12. A method for detecting contraband, said method comprising:

positioning an object within a field of view of an x-ray diffraction (XRD) system;

generating primary x-rays from a stationary x-ray source of the XRD system to scan the object, the stationary x-ray source including a plurality of x-ray focal spot locations in a linear arrangement;

collimating coherently scattered x-rays produced by an interaction of the primary x-rays with the object at a constant scatter angle using a secondary collimator;

receiving the collimated coherently scattered x-rays with a stationary detector to generate XRD data; and determining a probability of the contraband being present in the object by analyzing the XRD data.

13. The method of claim 12, wherein generating primary x-rays comprises generating the primary x-rays from a linear distributed x-ray source as parallel x-ray beams, the parallel x-ray beams being within a plane perpendicular to an axis of translation and projected towards the stationary detector; and wherein receiving coherently scattered x-rays comprises receiving the coherently scattered x-rays with the at least one detector having the linear arrangement substantially similar to an arrangement of the linear distributed x-ray source.

14. The method of claim 13, wherein the linear distributed x-ray source comprises at least one cathode module, the at least one cathode module comprising electron emitter elements including one of at least one field emitter element, at least one thermionic element, and at least one steered solitary electron beam source.

15. The method of claim 12, further comprising:

performing an initial scan of the object in a first scanning system to acquire a first set of data;

identifying at least one region of interest (ROI) in the object based on the acquired first set of data, the at least one ROI comprising at least a portion of the object;

passing the object to the XRD system positioned in-line with the first scanning system; and generating the primary x-rays from the stationary x-ray source based on the at least one identified ROI.

16. The method of claim 15, wherein generating primary x-rays comprises:

selecting at least one x-ray focal spot location from a plurality of x-ray focal spot locations of the stationary x-ray source, the at least one x-ray focal spot location having primary radiation beams that most closely intersect the at least one ROI; and electronically activating the at least one x-ray focal spot location using activations connections to an emitter element at the at least one x-ray focal spot location.

17. The method of claim 16, wherein electronically activating the at least one x-ray focal spot location comprises activating a plurality of specified x-ray focal spot locations in one of a queued activation patterned, a sequential activation pattern, and a concurrent activation pattern based on the at least one identified ROI.

18. A contraband detection system comprising a non-translational x-ray diffraction (XRD) system, the non-translational XRD system comprising:

a gantry having an opening to receive an object to be scanned, the object traversing through the gantry along an axis of translation;

a stationary distributed x-ray source affixed to a first side of the gantry and comprising a plurality of x-ray focal spot locations in a linear arrangement, the plurality of x-ray focal spot locations configured to project x-rays toward the object;

a stationary detector affixed to a second side of the gantry generally opposite the stationary distributed x-ray source and configured to measure a coherent scatter spectra of the x-rays after passing through the object, the stationary detector comprising at least one detector in a linear arrangement substantially similar to the linear arrangement of the plurality of x-ray focal spot locations; and a data acquisition system (DAS) connected to the stationary detector and configured to measure the coherent scatter spectra, the coherent scatter spectra utilized to determine a material composition of at least a portion of the object.

19. The contraband detection system of claim 18, wherein the stationary distributed x-ray source is configured to project the x-rays toward the object in a parallel beam pattern.

20. The contraband detection system of claim 18, wherein a length of the stationary detector along the gantry is equal to a length of the stationary distributed x-ray source along the gantry.

21. The contraband detection system of claim 18, further comprising a contraband detection apparatus positioned in-line with the XRD system and configured to perform a first scan of the object.

22. The contraband detection system of claim 21, wherein the XRD system comprises a computer programmed to:

receive object data from the contraband detection apparatus;

identify at least one region of interest (ROI) in the object based on the object data;

generate a desired scanning pattern for the XRD system for the at least one ROI; and cause the XRD system to scan the at least one ROI to acquire XRD data.

23. The contraband detection system of claim 22, wherein the computer is programmed to combine the object data and the XRD data to detect a presence of contraband in the object and, if the contraband is detected, assign a threat level and generate an alert.

* * * * *